United States Patent

Dekura et al.

Patent Number: 4,871,625
Date of Patent: Oct. 3, 1989

[54] SYNTHETIC LUBRICANT FOR LUBRICATING THIN FILM AND MAGNETIC RECORDING MEDIUM

[75] Inventors: Takateru Dekura, Kamakura; Juro Endo, Kumagaya, both of Japan

[73] Assignees: Hitachi Metals, Ltd.; Maruwa Bussan K.K., both of Tokyo, Japan

[21] Appl. No.: 174,410

[22] Filed: Mar. 28, 1988

[30] Foreign Application Priority Data

Apr. 16, 1987 [JP] Japan .................. 62-94122

[51] Int. Cl.$^4$ .............................. G11B 5/64
[52] U.S. Cl. .................... 428/695; 427/131; 428/694; 428/900
[58] Field of Search ............ 428/695, 694, 900; 427/131; 252/50

[56] References Cited

U.S. PATENT DOCUMENTS 4,018,967  4/1977  Roller ................ 428/900
4,536,444  8/1985  Sumiya ............... 428/695
4,613,548  9/1986  Lum ................... 428/900

FOREIGN PATENT DOCUMENTS 126627  6/1986  Japan .

*Primary Examiner*—Paul J. Thibodeau
*Attorney, Agent, or Firm*—Finnegan, Henderson, Farabow, Garrett & Dunner

[57] ABSTRACT

A synthetic lubricant for lubricating a thin film containing a phosphonitrile ester obtained by cyclic polymerization or ring opening polymerization and represented by the following general formula (I):

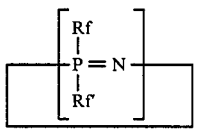

wherein n represents 3 to 10, and Rf and Rf' represent one or two groups selected from the following groups:

$Y(C_3F_6O)_l CFYCH_2O-$ $Y(C_3F_6O)_l (CF_2O)_m CFYCH_2O-$ $Y(C_2F_4O)_l (CF_2O)_m CFYCH_2O-$ $Y(CF_2)_l C_2H_4O-$ $Y(CF_2)_l CH_2O-$ $H(CF_2)_l CH_2O-$ wherein l represents 3 to 250, m 1 to 250, and Y one selected from the group consisting of F—, $CF_3$—, $C_2F_5$—, $CF_3O$—, $C_2F_5O$— and $C_3F_7O$—; and a magnetic recording medium coated with this lubricant.

4 Claims, No Drawings

SYNTHETIC LUBRICANT FOR LUBRICATING THIN FILM AND MAGNETIC RECORDING MEDIUM

BACKGROUND OF THE INVENTION

Field of the Invention

The present invention relates to a synthetic lubricant for lubricating a thin film and a magnetic recording medium and, more particularly, to a synthetic lubricant which is capable of firmly adhering to the surface of a substrate of metal, glass, ceramic, carbon or the like in the form of a thin film and providing it with good lubrication and a magnetic recording medium with a lubricant layer formed thereof by using such a lubricant.

The surface of a magnetic recording medium is coated with a lubricant, because lubrication is required between the magnetic recording medium and a magnetic head which come into contact with each other.

In the case of a thin film magnetic recording medium having a high recording density, a flying head is used as the magnetic head. The flying head is operated in the following manner. The flying head is pressed against the medium by the spring force of a load arm and a gimbal at a force of about 10 gf while the medium is not rotated. When the recording medium starts to rotate, the slider portion (made of MnZn ferrite, $Al_2O_3$—TiC, $ZrO_2$ or $CaTiO_3$) of the flying head slides on the medium, and when the rotation of the medium assumes a normal state (e.g., 3,600 rpm), the flying head floats at a height of 0.15 to 0.5 $\mu$m from the medium on a stream of air which moves together with the rotation of the medium. At this time, the flying head sometimes comes into contact with the surface of the medium due to the vibration applied from the outside or the unevenness of the surface of the medium. When the rotation of the medium is stopped, the flying head gradually approaches the medium and moves on the medium as if to be dragged or stops on the medium while bouncing thereon.

In order to improve the electromagnetic transducing characteristics between a magnetic recording medium and a flying head, it is desirable that the lubricant film applied to the surface of the medium is as thin as possible. When the lubricant film is several hundred Å thick, the flying head adheres to the surface of the medium, in other words, a sticking phenomenon is produced, thereby making it impossible to start to rotate the medium. Thus, it is desirable that the thickness of the lubricant on the surface of the medium is one of several molecular layers.

In order to resist the shock or wear of a flying head by means of the lubricant layer of one to several molecular layers, the lubricant is required not only to be excellent in lubricating properties but also to be firmly absorbed to the metal or carbon of the substrate of the medium.

As the lubricant, perfluoropolyethers are conventionally used and are commercially available as Fomblin produced by Montedison, Italy and Krytox produced by DuPont, U.S.A. These lubricants are disclosed in U.S. Pat. Nos. 3,242,218, 3,665,041, 3,715,378, etc.

Perfluoropolyethers are high-quality lubricating oils having excellent thermal stability, heat resistance and resistance to chemicals and low evaporation rate. However, they have very low adsorptivity, and when they are applied to the surface of metal, glass, ceramic, carbon or the like into a thickness of one to several molecular layers as a thin film lubricant, they cannot be firmly adsorbed to the surface of metal or the like. They are therefore limited as a lubricant for the above-described magnetic recording medium.

To improve the adsorptivity of a perfluoropolyether lubricant, attempts have been made on firmly adsorbing it to a magnetic recording medium by attaching a polar group to the end of the perfluoropolyoxyalkylene group and increasing the dipole mement of the polar group to a predetermined value or more. These proposals are disclosed in, for example, U.S. Pat. Nos. 4,267,238 and 4,268,556.

In a lubricant having a perfluoropolyoxyalkylene group with a polar group attached to the end thereof, the lubricant is adsorbed to metal or carbon by the polar group and the perfluoropolyoxyalkylene group extending from the polar group provides lubricating properties.

However, such a lubricant cannot satisfy the characteristics required when it is used as a lubricant for a thin film magnetic recording medium because the adsorptivity provided solely by the polar group is insufficient for the following reasons:

(1) A thin film magnetic recording medium is used in a very severe state in which the shock and sliding friction of a magnetic head are applied to the medium.

(2) The surface of the thin film magnetic recording medium is a thin film metal medium layer (e.g., Co—Ni layer) formed by sputtering or plating, or a protective film of carbon, ceramic or the like formed on the thin film metal medium layer. The bonding by the polar group cannot maintain sufficient strength between the lubricant layer and a film of such an inorganic material as metal, carbon and ceramic.

These facts bring about the following problems: the lubricant film formed on the surface of the magnetic recording medium peels off, or the molecules of the lubricant film are flown about or blown to the outer peripheral portion of the medium locally by the centrifugal force applied by the rotation of the magnetic recording medium (the characteristic of a lubricant film which cause these phenomena will be referred to as "migrating characteristic"), thereby making it impossible to maintain the lubricant thin film in a uniform state.

SUMMARY OF THE INVENTION

Accordingly, it is an object of the present invention to eliminate the above-described problems in the prior art and to provide a synthetic thin film lubricant which is capable of firmly adhering to the surface of an inorganic material such as metal, carbon, ceramic, glass in the form of a thin film and providing it with good lubrication.

It is another object of the present invention to provide a synthetic lubricant which has excellent lubricating properties and very high durability and adsorptivity.

It is still another object of the present invention to provide a lubricated magnetic recording medium which exhibits very good resistance to contact-start-stops (CBS) and desirable non-migrating characteristic.

The present invention provides a synthetic lubricant for lubricating a thin film containing a phosphonitrile ester obtained by cyclic polymerization or ring opening polymerization and represented by the following general formula (1):

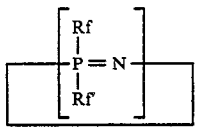
(I)

wherein n represents 3 to 10, preferably 3 to 5, and Rf and Rf' represent one or two groups selected from the following groups:

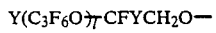

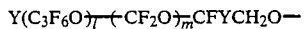

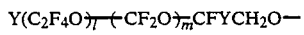

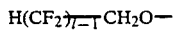

where l represents 3 to 250, m 1 to 250, and Y one selected from the group consisting of F—, $CF_3$—, $C_2F_5$—, $CF_3O$—, $C_2F_5O$— and $C_3F_7O$—; and a magnetic recording medium with said lubricant applied thereto.

DESCRIPTION OF THE PREFERRED EMBODIMENTS

The present invention will be explained in detail hereinunder.

A compound contained in a synthetic lubricant for lubricating a thin film according to the present invention is a phosphonitrile derivative, as represented by the general formula (I). In the formula (I) Rf and Rf' represent a polyfluoroalkoxy group or a polyfluorooxyalkylene alkoxy group.

In the formula (I), the molecular weight of Rf and Rf' is preferably 300 to 50,000. In the compound represented by the formula (I), Rf and Rf' are the portions which control the lubricating properties of the lubricant. If the molecular weight thereof is less than 300, the resistance to shock is lowered and the lubricating properties are deteriorated. As the molecular weight of Rf and Rf' increases, the lubricating properties are improved, but if the molecular weight becomes so large as to exceed 50,000, when the lubricant is dissolved in a solvent at the time of coating, it takes the form of an emulsion, thereby making uniform coating difficult due to high viscosity. In addition, when such a lubricant is applied to a magnetic recording medium, it disadvantageously produces sticking between the medium and a magnetic head which is a disadvantage.

Rf and Rf' may be either the same or different.

In the formula (I), n is an integer of 3 to 10. That is, the number of the phosphonitrile groups subjected to cyclic or ring opening polymerization and contained in the compound represented by the formula (I) is preferably 3 to 5.

A compound having not less than 10 phosphonitrile groups is impracticable because it is close to a polymeric rubber-like compound which is difficult to dissolve in a solvent.

A compound represented by the formula (I) is produced, for example, by the following methods.

Synthesis 1

200 ml of trichlorotrifluoroethane dried over anhydrous sodium sulfate was charged into a 500-ml four-necked flask equipped with a stirrer, a thermometer, a reflux condenser and a dropping funnel. 5.0 g (0.125 mol) of sodium hydroxide was added dropwise thereto, and to the thus-formed slurry mixture, 250 g (0.1 mol) of polyfluorooxyalkylene alcohol [formula: $F(C_3F_6O)_l—C_2F_4CH_2OH$, average molecular weight: 2,500 (measured by nuclear magnetic resonance analysis)] was added and stirred for 1 hour. The uniformly stirred slurry was heated by a mantle heater for 22 hours to dissolve sodium hydroxide. After trichlorotrifluoromethane was distilled off, the solvent was substituted by 200 ml of perchlorodimethyl cyclohexane. To this solution, 5.8 g (0.016 mol) of a phosphonitrile chloride trimer [formula: $(PCl_2N)_3$] dissolved in 100 ml of xylene was added dropwise in 30 minutes, and the mixture was heated under stirring to carry out reaction under reflux for 96 hours. After the reaction, the mixture was cooled and sodium chloride was filtered out. The residue was washed with distilled water and then dehydrated. When the solvent was distilled off, an oily matter was obtained.

In the IR spectrum analysis of the oily matter, the peak of alcohol at 3500 cm$^{-1}$ was slight, and peaks appeared in the vicinities of 1424, 1091, 971 and 885 cm$^{-1}$, which were considered to be a combination of C—O—P, and the structure of a triphosphonitrile ester was shown. It was confirmed that the oily matter was

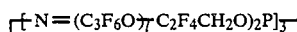

wherein l is 14 to 15 on the average.

Synthesis 2

In the same way as in Synthesis 1, 11 g (0.275 mol) of sodium hydroxide was added dropwise to 250 ml of trichlorotrifluoroethane which had been dried over anhydrous sodium sulfate and charged into a 500-ml four-necked flask. To the thus-formed slurry mixture, 180 g (0.040 mol) of polyfluorooxyalkylene alcohol [formula: $F(C_3F_6O)_l—C_2F_4CH_2OH$, average molecular weight: 4,500 (measured by nuclear magnetic resonance analysis)] and 80 g (0.219 mol) of perfluoroalkyl ethanol (formula: $C_6F_{13}C_2H_4OH$) were added and stirred for 22 hours under reflux. After the reaction mixture was cooled, trichlorotrifluoroethane was substituted by 200 ml of perfluorodimethyl cyclohexane. To this solution, 15 g (0.043 mol) of a phosphonitrile chloride trimer [formula: $(PCl_2N)_3$] dissolved in 100 ml of xylene was added dropwise in 30 minutes, and the mixture was reacted under reflux for 96 hours by using a mantle heater. After the reaction mixture was cooled, the solid matter was filtered out. The residue was washed with distilled water and sodium chloride was removed. The solution was then dehydrated and the solvent was distilled off to obtain an oily matter.

In the IR spectrum analysis of the oily matter, the peak of alcohol at 3500 cm$^{-1}$ disappeared, and peaks appeared at 1424, 1091, 971 and 885 cm$^{-1}$, which exhibited a combination of C—O—P, and the structure of a triphosphonitrile ester was shown. It was confirmed that the oily matter was

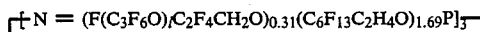

wherein l is 26 to 27 on the average.

Synthesis 3

In the same way as in Syntheses 1 and 2, 26.0 g (0.65 mol) of sodium hydroxide was added dropwise to 200 ml of diethyl ether which had been dried over anhydrous sodium sulfate and charged into a 500-ml four-necked flask. To the thus-formed slurry mixture, 165 g (0.355 mol) of polyfluoroalcohol $F(CF_2)_8C_2H_4OH$ and 65 g (0.280 mol) of polyfluoro alcohol $H(CF_2)_4CH_2OH$ were added and stirred for 22 hours under reflux. After diethyl ether was distilled off, the solvent was substituted by 200 ml of xylene. To this solution, 37 g (0.106 mol) of a phosphonitrile chloride trimer [formula: $(PCl_2N)_3$] dissolved in 100 ml of xylene was added dropwise in 30 minutes, and the mixture was stirred under reflux for 96 hours. After the reaction mixture was cooled, the solid matter was filtered out. The residue was washed with distilled water and dehydrated. The solvent was distilled off to obtain a pasty matter.

In the IR spectrum analysis of the oily matter, the peak of alcohol at 3500 cm$^{-1}$ disappeared, and peaks appeared at 1424, 1091, 971 and 885 cm$^{-1}$, which exhibited a combination of C—O—P, and the structure of a triphosphonitrile ester was shown. It was confirmed that the pasty matter was

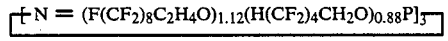

In any of the above-described syntheses, an alkali fusion method was adopted, but an alcohol may be reacted with phosphonitrile chloride after it has been changed into polyfluoroalkoxy sodium or polyfluorooxyalkylene alkoxy sodium by using metallic sodium.

These and other synthetic lubricants for lubricating a thin film of the present invention are very effective as a lubricant for coating a thin film magnetic recording medium for high-density thickness recording material or the like. They form a lubricant film of having a thickness one to several molecular layers.

When coating, a lubricant of the present invention is preferably dissolved in a solvent such as trichlorotrifluoroethane so that the concentration of the compound represented by the formula (I) is about 0.01 to 0.02 vol%.

A magnetic recording medium which is to be coated with a lubricant of the present invention is composed of a hard discal substrate, and at least a magnetic recording layer and a protective film layer for covering the magnetic recording layer formed thereon. The substrate is made of any given material such as aluminum, aluminum alloy, ceramic and glass. A further film is formed on the substrate, if necessary, which film preferably is a hard film. More preferably, the hard film formed on the substrate, if necessary, is of chromium, Ni—P, Ni—Cu—P, anodized aluminum or the like. As the magnetic recording layer, various kinds of magnetic layers may be adopted, for example, Co, Co—Ni, Co—Ni—Cr, Co—Ni—Pt, Co—Ni—P, or Co—Pt. As the protective film layer, carbon and/or silicon oxide are preferable and, above all, graphite or amorphous carbon is more preferable.

A compound represented by the general formula (I) and contained in a synthetic lubricant for lubricating a thin film has 3 to 10, preferably 3 to 5, phosphonitrile groups at a substantially central part of the bond chain. Since —P=N— of the phosphonitrile group is an inorganic material and firmly adheres to the surface of an inorganic material such as a metal or carbon and, in addition, since a plurality of chains of phosphonitrile groups are bonded, it is possible to obtain a large bond area. The central portion of the compound is absorbed to the surface of a metal or the like by electrons, as described above, and the Rf and Rf' groups at both ends thereof reach the positions far from the surface, the Rf and Rf' groups producing a good lubricating effect.

A synthetic lubricant for lubricating a thin film therefore has not only excellent lubricating properties but also very high durability and adsorptivity. A lubricant of the present invention is very effective for forming a lubricating film on a high-density magnetic recordng medium and the like, and a magnetic recording medium with such a lubricant adhered to the surface thereof exhibits very excellent resistance to CSS and desirable migrating characteristics.

Examples and comparative examples will be shown in the following.

EXAMPLES 1 TO 3

Aluminum substrate disks of 5¼" diameter were produced by each of the following methods (1) to (5). The surfaces of the thin film disks with carbon protective films formed thereon was uniformly coated with later-described compounds which had been diluted to 0.01 vol% with trichlorotrifluoroethane by spraying so as to form lubricant films. The properties of the lubricant films were tested. The results are shown in Table 1.

Producing Method (1) an aluminum substrate subjected to anodization treatment was treated with polished texture of obtain a substrate having an average surface roughness Ra of 0.02 μm. A sputtered film of CoNiCr (13 at% of Ni, 3 at% of Cr and the balance Co) was formed into a thickness of 1,000 Å on the thus-obtained substrate in an argon atmosphere containing nitrogen. A carbon protective film was formed thereon into a thickness of 200 Å by DC sputtering. The thus-obtained medium was then subjected to heat treatment in vacuum at 340° C. for 2 hours to obtain a magnetic disk.

(2) An aluminum substrate with a chromium underlayer of 2,000 Å thick formed thereon by sputtering was treated with polished texture to obtain a substrate having an average surface roughness Ra of 0.02 μm. A sputtered film of CoNiCr (13 at% of Ni, 3 at% of Cr and the balance Co) was formed into a thickness of 800 Å on the substrate in an argon atmosphere containing nitrogen. A carbon protective film was formed thereon into a thickness of 200 Å by DC sputtering to obtain a magnetic disk.

(3) An aluminum substrate plated with NiP was treated with polished texture to obtain a substrate having an average surface roughness Ra of 0.02 μm. A sputtered film of CoNiPt (15 at% of Ni, 7 at% of Pt and the balance Co) was formed into a thickness of 800 Å on the substrate in an argon atmosphere. A carbon protective film was formed thereon into a thickness of 200 Å by DC sputtering to obtain a magnetic disk.

(4) On the substrate obtained in the same way as in the method (3), a CoNiPt film (15 at% of Ni, 7 at% of Pt and the balance Co) was formed into a thickness of 800 Å by plating. A carbon protective film was formed thereon into a thickness of 200 Å by DC sputtering to obtain a magnetic disk.

(5) On the substrate obtained in the same way as in the method (1), a sputtered $Fe_3O_4$ film containing Co was formed by RF sputtering. The thus-obtained medium was then subjected to heat treatment in an atmosphere at 320° C. for 2 hours to obtain a $\gamma$-$Fe_2O_3$ film of 1,500 Å thick. A carbon protective film was formed thereon into a thickness of 200 Å by DC sputtering to obtain a magnetic disk.

COMPOUND FOR A LUBRICANT

EXAMPLE 1

Triphosphonitrile obtained in synthesis 1

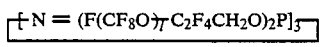

where l is 14 to 15 on the average, and the average molecular weight of the polyfluorooxyalkylene alkoxy group is 2,500.

EXAMPLE 2

Triphosphonitrile obtained in Synthesis 2

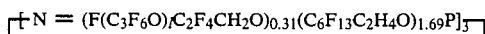

where l is 26 to 27 on the average, the average molecular weight of the polyfluorooxyalkylene alkoxy group is 4,500, the average molecular weight of the polyfluoroalkoxy group is 363, and the average molecular weight of these alkoxy groups is 1,004.

Example 3

Triphosphonitrile obtained in Synthesis 3

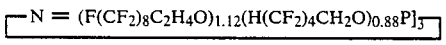

wherein the molecular weights of the fluoroalkoxy groups are 463 and 231, respectively, and the average molecular weight is 361.

The properties of the lubricant films were tested in the following way:

Resistance to CSS

The resistance to CSS was examined by the number of times of CSS repeated until the head was stuck or crushed by using a mini-winchester head of MnZn ferrite under the following conditions: flying height hf=0.3 $\mu$m, 3,600 rpm, and an on-off cycle of 15 sec (15-sec on and 15-sec off).

Migrating characteristics

The thickness of the lubricant film was measured at a point of R (radius)=50 mm before driving and after one-month continuous driving at 3,600 rpm by FTIR (Fourier transformed infrared spectrophotometry). The migrating characteristic was represented by the reduction ratio (%) of film thickness after driving with respect to the film thickness before driving.

Comparative Examples 1 to 4

Lubricant films were formed in the same way as in Example 1 except that the following compounds which had been diluted to 0.02 vol% with trichlorotrifluoroethane were spray coated as the lubricants. The properties of the lubricant films were tested. The results are shown in Table 1.

Comparative Example 1

Fomblin Z-25 (produced by Montedison, Molecular weight: 15,000)

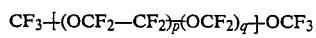

wherein p/q=50/1

Comparative Example 2

Fomblin YR (produced by Montedison, molecular weight: 6,500)

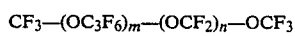

wherein m/n=40/1

Comparative Example 3

Krytox 143 AC (produced by Du Pont, Molecular weight: 6,500)

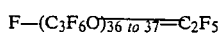

Comparative Example 4

Krytox 157 FS-M (produced by Du Pont, molecular weight: 4,500)

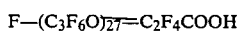

TABLE 1

| Example | Resistance to CSS (Kilo cycles) | | | | | Migrating Characteristics (%) | | | | |
|---|---|---|---|---|---|---|---|---|---|---|
| Disk No. | 1 | 2 | 3 | 4 | 5 | 1 | 2 | 3 | 4 | 5 |
| Example | | | | | | | | | | |
| 1 | 50 | 60 | 75 | 80 | 100 | <10 | <10 | <10 | <10 | <10 |
| 2 | 60 | 65 | 70 | 70 | 80 | <10 | <10 | <10 | <10 | <10 |
| 3 | 35 | 38 | 43 | 45 | 60 | <10 | <10 | <10 | <10 | <10 |
| Comparative Example | | | | | | | | | | |
| 1 | 20 | 19 | 18 | 15 | 18 | 20 | 30 | 35 | 30 | 30 |
| 2 | 10 | 11 | 13 | 10 | 12 | 70 | 60 | 70 | 70 | 60 |
| 3 | 10 | 14 | 13 | 11 | 17 | 50 | 35 | 40 | 45 | 40 |
| 4 | 18 | 20 | 20 | 15 | 17 | 30 | 20 | 35 | 30 | 30 |

As is clear from Table 1, in any disk using a lubricant in Example 1 or 2, the resistance to CSS is as high as 50 to 100 kilo cycles, and the reduction ratio of the film thickness after the migrating characteristic test is as small as 10% or less.

The lubricant in Example 3 produces no problem in the migrating characteristic test, but since the molecular weight of the alkoxy group is 500 or less, the resistance to CSS is a little inferior.

On the other hand, in the conventional lubricants in Comparative Examples 1 to 4, the resistance to CSS is as low as 10 to 20 kilo cycles, and the reduction ratio of the film thickness after the migrating characteristic test is as large as 30 to 60%. Thus, it has been proved that the adsorptivities of these lubricants with respect to a carbon protective film are very low. This is considered to be because the resistance to CSS is inferior due to a large amount of migration in spite of a large molecular weight.

Although the above experiments were conducted with a carbon protective layer, the lubricant of the present invention was proved to have a strong adsorptivity to silicon oxide, glass and metal as well.

Accordingly, it is clear that the lubricant of the present invention has much higher resistance to CSS, more desirable migrating characteristic and better lubricating properties than the conventional ones, and that it can sufficiently meet the properties required of a thin film magnetic disk.

While there has been described what are at present considered to be preferred embodiments of the invention, it will be understood that various modifications may be made thereto, and it is intended that the appended claims cover all such modifications as fall within the true spirit and scope of the invention.

What is claimed is:

1. A synthetic lubricant on a magnetic thin film recording medium, said lubricant containing a phosphonitrile ester obtained by cyclic polymerization or ring opening polymerization and represented by the following formula (I):

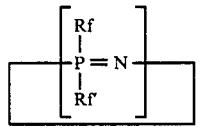

wherein n represents 3 to 10, and Rf and Rf' represent one or two groups selected from the following groups:

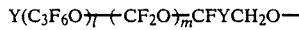

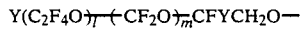

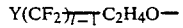

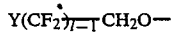

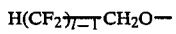

wherein the molecular weight of Rf and Rf' is 300 to 50,000 and wherein l represents 3 to 250, m represents 1 to 250, and Y represents a member selected from the group consisting of F—, CF$_3$—, C$_2$F$_5$—, CF$_3$O—, C$_2$F$_5$O— and C$_3$F$_7$O— and an intermediate protective film between the lubricant and the magnetic thin film layers.

2. A lubricant according to claim 1, wherein the molecular weight of the alkoxy group is more than 500.

3. A synthetic lubricant on a magnetic thin film recording medium, said lubricant a thin film containing a phosphonitrile ester obtained by cyclic polymerization or ring opening polymerization and represented by the following formula (I):

wherein n represents 3 to 10, and Rf and Rf' represent one or two groups selected from the following groups:

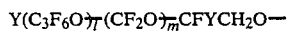

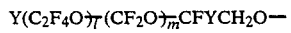

wherein the molecular weight of Rf and Rf' is 300 to 50,000 and wherein l represents 3 to 250, m represents 1 to 250, and Y represents a member selected from the group consisting F—, CF$_3$—, C$_2$F$_5$, CF$_3$O—, C$_2$F$_5$O—, and C$_3$F$_7$O— and an intermediate protective film between the lubricant and the magnetic thin film layers.

4. A lubricant according to claim 3 wherein the molecular weight of the alkoxy group is more than 500.

* * * * *